(12) United States Patent
Montone et al.

(10) Patent No.: US 11,815,884 B2
(45) Date of Patent: Nov. 14, 2023

(54) MACHINE LEARNING-BASED QUALITY CONTROL OF A CULTURE FOR BIOPRODUCTION

(71) Applicant: LYNCEUS SAS, Paris (FR)

(72) Inventors: Guglielmo Montone, Sceaux (FR); Severin Limal, Paris (FR)

(73) Assignee: LYNCEUS, SAS, Paris (FR)

( * ) Notice: Subject to any disclaimer, the term of this patent is extended or adjusted under 35 U.S.C. 154(b) by 0 days.

(21) Appl. No.: 18/103,598

(22) Filed: Jan. 31, 2023

(65) Prior Publication Data

US 2023/0168667 A1 Jun. 1, 2023

Related U.S. Application Data

(63) Continuation of application No. 17/826,682, filed on May 27, 2022, now Pat. No. 11,567,488.

(60) Provisional application No. 63/193,675, filed on May 27, 2021.

(51) Int. Cl.
*G05B 23/02* (2006.01)
*G06F 18/214* (2023.01)
*G06N 3/04* (2023.01)
*G06N 3/08* (2023.01)

(52) U.S. Cl.
CPC ....... *G05B 23/024* (2013.01); *G05B 23/0221* (2013.01); *G06F 18/214* (2023.01); *G06N 3/04* (2013.01); *G06N 3/08* (2013.01)

(58) Field of Classification Search
CPC .. H03M 7/6064; H03M 7/6011; G06N 3/088; G06N 3/084; G06N 3/0454; G06N 3/08; G06N 20/00
See application file for complete search history.

(56) References Cited

U.S. PATENT DOCUMENTS

| | | | |
|---|---|---|---|
| 2021/0334656 A1* | 10/2021 | Sjögren | G05B 23/024 |
| 2021/0380910 A1* | 12/2021 | Chen | G06T 7/11 |
| 2021/0382050 A1* | 12/2021 | Shea | G01N 33/564 |
| 2022/0068440 A1* | 3/2022 | Mrziglod | G05B 13/048 |
| 2022/0157403 A1* | 5/2022 | Mason | G16B 20/20 |
| 2022/0215900 A1* | 7/2022 | De La Vega | G16B 20/20 |

OTHER PUBLICATIONS

Anh et al., Biotherapeutic Products, Cellular Factories, and Multiomics Integration in Metabolic Engineering (Year: 2020).*

(Continued)

*Primary Examiner* — Mohammad K Islam
(74) *Attorney, Agent, or Firm* — David H. Judson

(57) ABSTRACT

Real-time quality control of a culture for bioproduction is facilitated using machine learning. In this approach, real-time process data for a set of parameters for a current production run is received. Based on this process data, a prediction is made using an instance of a machine learning model that has been trained on process data from past production or development runs. The instance is uniquely associated to a particular culture day and thus independent of any other instance of the machine learning model (for other culture days). Based on the prediction, a quality control recommendation for the current production run is then made. Several different types of predictions are enabled, and various different recommendations are provided based on the predictions.

17 Claims, 4 Drawing Sheets

(56) References Cited

OTHER PUBLICATIONS

Borkowski et al., Large scale active-learning-guided exploration for in vitro protein production optimization (Year: 202).*
Möller et al., Digital Twins for Tissue Culture Techniques—Concepts, Expectations, and State of the Art (Year: 2021)*
Charaniya et al., Mining bioprocess data: opportunities and challenges (Year: 2008).*
Bachinger et al., Searching for process information in the aroma of cell cultures, (Year: 2000).*

* cited by examiner

MACHINE LEARNING-BASED QUALITY CONTROL OF A CULTURE FOR BIOPRODUCTION

BACKGROUND

Technical Field

This application relates generally to real-time quality control of a culture for bioproduction, e.g., in a bioreactor or fermenter.

Background of the Related Art

Biological production of cell cultures in bioreactors is slow, expensive and subject to failure and variability. Among other solutions, it is known to predict outcomes of these types of manufacturing processes using process models. In this type of approach, historic data related to past process runs for manufacturing a sample are accessed and compared against data from a current process run of the process and that is based on a selected process model. The current data typically comprises process strategy data, bioreactor instrument data, and data from online or offline sensors. Based on the comparison, an outcome of at least one selected parameter of the current process run is made. Other such techniques have been used to create time-based predictive models for various process variables including Total Cell Density (TCD), Viable Cell Density (VCD), osmolality and others.

While techniques such as described above provide advantages, there are many factors that can create challenges in modeling of this type. The most significant challenge is data variability, as manufacturers typically use many bioreactors and for different types of cultures, and they operate these reactors for both development and production runs. The resulting data, which often corresponds to a large number of disparate runs, is highly unbalanced and often incomplete, as many days in the culture have missing data. Historic data of this type may cover many years of development and production operations, as well as be obtained across multiple locations. A further complication is that even the individual data collected comprises many different features. Building accurate predictive models in such circumstances has proven to be very challenging.

There remains a need to provide enhanced predictive solutions that address these problems and that facilitate increased production and cost savings in biological production systems.

BRIEF SUMMARY

Real-time quality control of a culture for bioproduction is facilitated using machine learning. In this approach, real-time process data for a set of parameters for a current production run is received. Based on this process data, a prediction is made using an instance of a machine learning model that has been trained on process data from past production or development runs. Preferably, the instance is uniquely associated to a particular culture day and thus is independent of any other instance of the machine learning model (for other culture days). Based on the prediction, a quality control recommendation for the current production run is then made. In one use case, the prediction indicates that the current production run is expected to fail, in which case the quality control recommendation is a recommendation to terminate the current production run early. In another use case, the prediction is an end day for the current production run being successful and is based on a given value of at least one parameter being reached, in which case the quality control recommendation is a recommendation to terminate the current production run on the end day. As another example use case, the instance of the machine learning model generates a list of parameters and their associated contribution to the prediction, and wherein the prediction identifies at least one parameter in the list whose adjustment is expected to enable early completion of the current production run; in such case, the quality control recommendation is a recommendation to adjust the at least one parameter in the list according to an identified value.

The foregoing has outlined some of the more pertinent features of the disclosed subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the disclosed subject matter and the advantages thereof, reference is now made to the following descriptions taken in conjunction with the accompanying drawings, in which.

DETAILED DESCRIPTION

Figure 1:
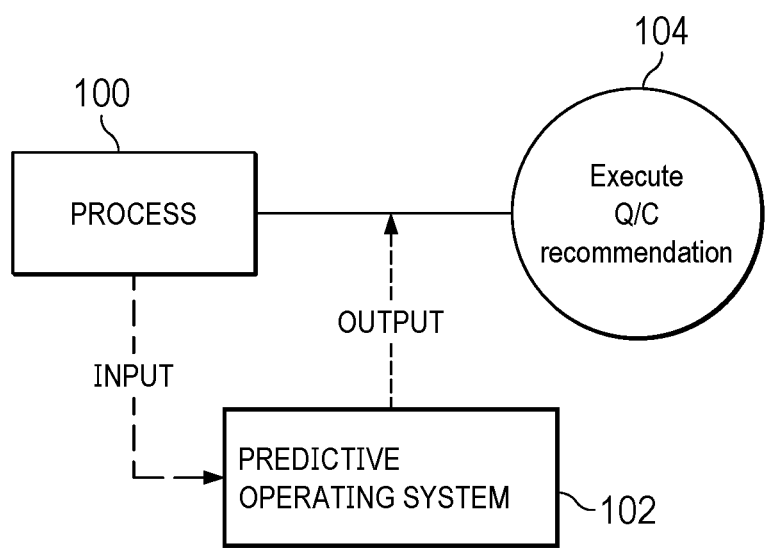
FIG. 1 depicts how the techniques of this disclosure may be implemented as a testing platform in association with a biological process having a bioreactor used to manufacture a cell culture.

FIG. 1 depicts a simplified representation of the basic operation of the technique of this disclosure for providing real-time quality control over the production of a culture in a bioproduction, such as in a bioreactor or a fermenter. Typically, the culture is a cell culture that is being cultivated in a current production run in the bioreactor or fermenter. In the drawing, the bioproduction is represented as process 100. As shown, real-time production data obtained from the process 100 is provided as input to a predictive operating system 102. The predictive operating system 102 is described in detail below. It includes at least one machine learning model having a set of "instances," with each instance corresponding to a particular period of time (typically, a culture "day"). Representative input data typically comprises process variables. The input data received from the process 100 is processed by the predictive operating system 102 to generate one or more predictions from which one or more quality control recommendations are then made. In particular, and in one use case, the prediction indicates that the current production run is expected to fail, in which case the quality control recommendation is a recommendation to terminate the current production run early. In another use case, the prediction is an end day for the current production run being successful and is based on a given value of at least one parameter being reached, in which case the quality control recommendation is a recommendation to terminate the current production run on the end day. As another example use case, the instance of the machine learning model generates a list of parameters and their associated contribution to the prediction, and wherein the prediction identifies at least one parameter in the list whose adjustment is expected to enable early completion of the current production run; in such case, the quality control recommendation is a recommendation to adjust the at least one parameter in the list according to an identified value. The one or more output(s) from the predictive operating system 102 are then provided to facilitate execution of the quality control recommendation, which is depicted as reference 104. The quality control recommendation typically is executed in an automated manner, e.g., by executing tooling, systems, devices or other control functionality in the process environment, as will be described in more detail below (see, the Examples). In this manner, the predictive operating system 102 facilitates increased production and cost savings, in real-time and with minimal process/production disruption.

Figure 2:
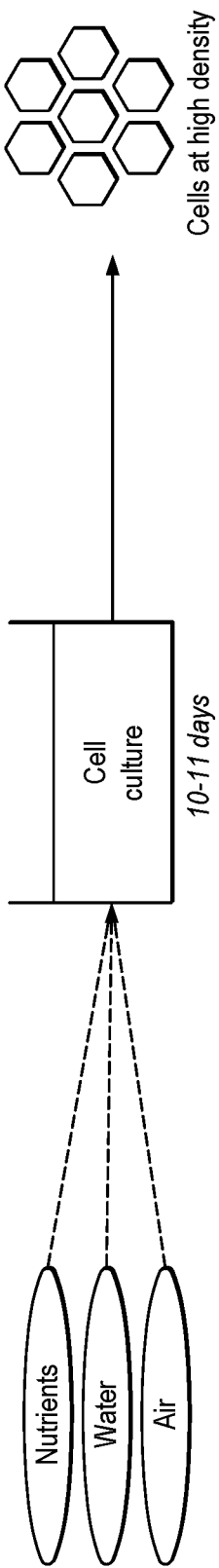
FIG. 2 depicts a biological process whose outcomes are desired to be predicted by the controller of this disclosure.

FIG. 2 depicts a representative biological process. In this example, various inputs (nutrients, water, air, etc.) 200 are supplied to a bioreactor 202 in which a cell culture is being grown over a time period (e.g., 10-11 days in this example). As the cell culture grows, various process variables (e.g., pH, temperature, lactate, glutamate, amino acid production, Viable Cell Density (VCD), Total Cell Density (TCD), etc.) are monitored, typically on a daily basis. At the end of a successful run, and as depicted at 204, cells at high density are produced. A process of this type can be modeled by various process parameters including, without limitation, VCD, TCD, cell diameter, and others.

In particular, and as described above, the predictive operating system comprises at least one machine learning model having a set of instances. The machine learning model is trained using process data collected from past production runs, past development runs, and combinations of such past production and development runs (collectively, the "historical" process data). According to an aspect of this disclosure, and in lieu of using a single machine learning model for the overall process, an "instance" of the machine learning model is generated for a particular culture day of the process that is operating over a period of such days. In other words, the process has a first instance of the machine learning model corresponding to a first culture day, a second instance of the machine learning model corresponding to a second culture day, and so forth. The culture days need not be continuous, although they typically are. Thus, in this example where there are 10-11 culture days, preferably there are as many instances of the machine learning model. Further, preferably each instance of the machine learning model is independent of any other instance. Typically, this independence is achieved by the manner in which each instance is trained. By way of example, assume instance number five (corresponding to day 5) is trained using the historical process data for days 1 through 4, wherein instance number six (corresponding to day 6) is then trained, say, using the historical process data received from days 1 through 5, and so forth. This is just a representative example that is not intended to be limiting.

As used herein, the notion of a "culture day" also is not intended to be limited, as the particular time period over which a culture is grown may vary and be less than a single calendar day (e.g., over a period measured in hours). In such context, the predictions provided by the modeling are simply periodic portions of the overall anticipated culture period. Further, it is not required that each culture day (or portion thereof) be the same time period across all training instances. For convenience, the remainder of the following description refers to the notion of a culture "day" with the understanding that this is merely for descriptive purposes.

Model Training

As noted above, typically a machine learning model used by the predictive operating system herein is trained off-line, i.e., prior to its use in providing real-time predictions, and generally the training data used to train the model comprises historical process data e.g., from prior production and/or development runs of the bioproduction equipment. It is not required that the historical data be received from the same bioproduction equipment or facility for which the predictions are to be made, although this will be the usual situation. Typically, a model used for prediction of a particular feature (such as VCD) is associated with a given culture process, although the model may itself leverage knowledge (via sequential and/or nested modeling) from other related models, as will be described below.

As also noted above, and during the typical production of a cell culture in a given bioreactor, a number of process parameters are obtained. For example, and for a particular culture day, and depending on the type and nature of the culture, parameters include, without limitation: VCD, temperature, PH, amino acid levels, glucose levels, and many more. For a typical culture day, there may be 10-15 different parameters values collected. Moreover, as the process continues over a period of days, additional parameters may be added to an initial parameter set. Typically, some of the parameters are dependent on one another, while others are independent of one another. As also previously described, and for every culture day for which a prediction is to be made, an instance (that is process-specific) of the model for that given culture day is created. More formally, and during the model training phase, the process data (FIG. 1, "input data") received by the predictive operating system for training purposes for a given process includes a historical data set (e.g., in the form of an input vector) comprising a set of process variables and the associated measured values that were obtained from the bioreactor as the cell culture is grown. Generalizing, this data thus represents the conditions that existed within the bioreactor at the time of the sampling. As noted, the input data is historical process data, and typically there is a set of such input data for each culture day.

During training of a particular machine learning model instance, preferably the full data set (all parameters and their associated values) for a given culture day, which is often of high dimension, is first subjected to an operation that reduces the number of dimensions. For example, the various data elements (or some subset thereof) may be concatenated together and thus flattened into a single dimension, thereby reducing the amount of data used to train the process-specific daily model (the machine learning model instance) for that culture day. The nature and scope of this data reduction operation may emphasize certain process parameters over others, and it may also take advantage of any feature importance analysis that may carried out to identify the contribution of a specific parameter with respect to a prediction. The dimension reduction may be deterministic or itself carried out using a neural network (e.g., a convolutional neural network (CNN)). A representative type of feature importance analysis that may be utilized in this manner is described in more detail below. Generalizing, and according to this aspect, either a priori or learned knowledge (or some combination thereof) is utilized to identify a feature set that identifies relationships between one or more of the process parameters reflected in the input vector; in this manner, the input vector (e.g., comprising ten (10) or more distinct process parameters) is compressed into a dimensionally-reduced vector (e.g., comprising just one or more process variable relationships) that the model learns are predictive or that are otherwise defined to reduce the amount of noise in the created model.

According to one implementation, the process-specific model for a given culture day is a machine learning model that is trained on the above-described data set(s). A machine learning model may be a feedforward-based recurrent neural network (RNN), although this is not a limitation. Formally, a NN of this type is a function g: X→Y, where X is an input space, and Y is an output space representing a categorical set in a classification setting (or a real number in a regression setting). For a sample x that is an element of X, $g(x) = f_L(f_{L-1}(\ldots((f_I(x))))$. Each $f_i$ represents a layer, and $f_L$ is the last output layer. The last output layer creates a mapping from a hidden space to the output space (class labels) through a softmax function that outputs a vector of real numbers in the range [0, 1] that add up to 1. The output of the softmax function is a probability distribution of input x over C different possible output classes. In a representative embodiment, an RNN with one hidden layer is used. Other machine learning algorithms that be leveraged include, without limitation, vector autoregressive modeling (e.g., Autoregressive Integrated Moving Average (ARIMA)), state space modeling (e.g., using a Kalman filter), a Hidden Markov Model (HMM), recurrent neural network (RNN) modeling, RNN with long short-term memory (LSTM), Random Forests, Generalized Linear Models, Extreme Gradient Boosting, Extreme Random Trees, and others. By applying these modeling techniques, new types of features are extracted, e.g., as follows: model parameters (e.g., coefficients for dynamics, noise variance, etc.), latent states, and predicted values for a next couple of observation periods.

Sequential and Nested Modeling

Figure 3:
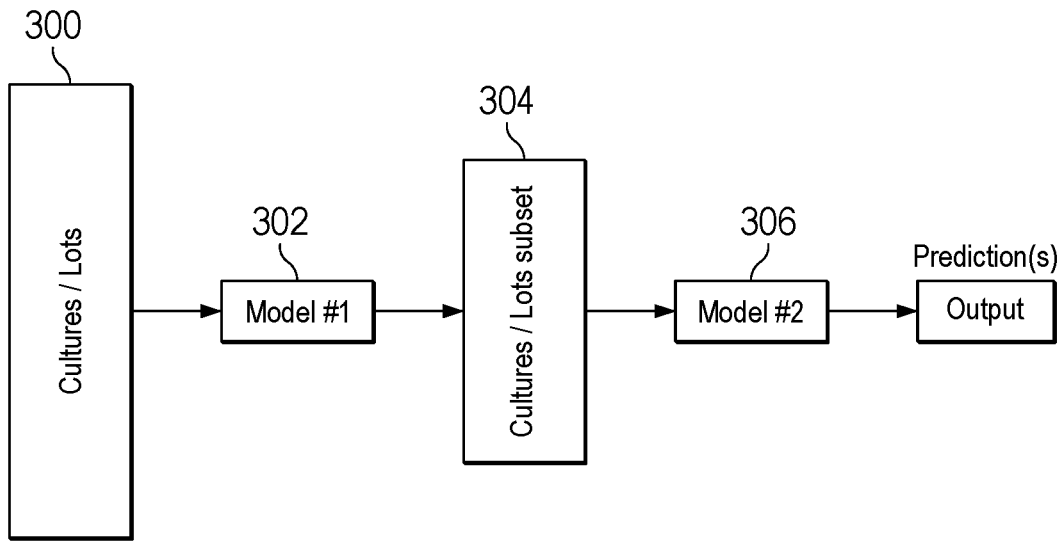
FIG. 3 depicts an example of how sequential modeling is used to facilitate training of predictive machine learning model instances according to an aspect of this disclosure.

According to a further aspect of this disclosure, a particular machine learning model instance for a given culture day may be built using nested or sequential modeling techniques, or combinations thereof. Sequential modeling is depicted in FIG. 3. In this example, the historical process data 300 is first classified according to a first machine learning model 302 to identify a subset 304 of the historical process data that meets some criteria, requirement or objective. For example, the subset 304 of the historical process data may represent the past production or development runs that have been classified by the first machine learning model 302 as representing a given outcome, such as being successful, or that otherwise correspond to a certain type. The subset 304 of the historical process data that meets the criteria, requirement or objective (as determined by the first machine learning model), is then used to train machine learning model 306, which corresponds to the "instance" described above. In other words, and using sequential modeling in this manner, the instance of the machine learning model 306 is only trained on process data from past production or development runs that have been classified by the first machine learning model 302 according to a certain type or having generated a given outcome.

To provide a concrete example, the first machine learning model 302 may be a Gaussian Mixed Model (GMM) that is developed to represent complex high dimensional data into a low-dimension space. In particular, a GMM is a probabilistic model that assumes all the data points are generated from a mixture of a finite number of Gaussian distributions with unknown parameters. In this modeling, a value is generated for each run, corresponding to its position relative to other runs in a multivariate space. Based on a threshold value and categorical labels within the supplied training data, runs are then identified as "failed" or "successful." In this example, the "successful" runs then represent the subset of the historical process data output from the first model 302. In other words, and using GMM as a classifier, successful runs (from a set of run data) are first identified. Based on these successful runs, the prediction(s) are generated using the machine learning model instances. Thus, in this example scenario the GMM model is used as a front-end to the instance-based modeling so as to constrain the latter to be based only a what the GMM model predicts are successful runs.

Figure 4:
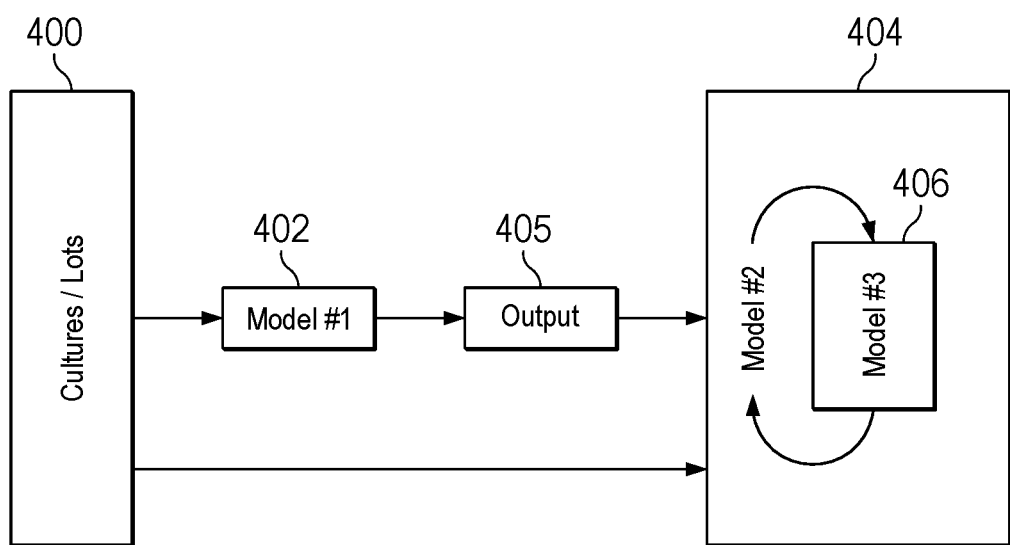
FIG. 4 depicts an example of how nested modeling is used to facilitate training of the predictive machine learning model instances.

Nested modeling (which may include embedded sequential models as well) is depicted in FIG. 4. In this example, there are several machine learning models 402, 404 and 406. The historical process data 400 is used to train machine learning model 402 to generate an output 405. Along with the historical process data 400, the output 405 is also provided to train machine learning model 404, which corresponds to a model instance for a particular culture day. Generalizing, a model is run first and values generated in output (from the first model) are then used to run another different model. One particular example of this approach inserts the GMM distribution values (for successful runs) into the instance prediction by including these distribution values as parameters in the input vector used to train the model instance. This is an example of nested and sequential modeling.

In some cases, and as also shown in FIG. 4, the output of a model, e.g., model 404, is used to generate another model, e.g., model 406, whose output is then fed back to update the output of the model 404, and wherein this looping process can continue to further refine an output or enable further modeling. An example of this approach is a permutation analysis (for feature importance), wherein a model is run within re-runs of the prediction to measure an importance of each individual parameter; comparisons are then carried out with respect to the original prediction (that does not take such feature importance into consideration). This is an example of sequential then nested modeling. To provide additional detail regarding this last example, the permutation analysis is used to shuffle values for each parameter across culture runs (while maintaining the timing of the parameter value) to preserve the distribution and statistical characteristics of the data but rendering that particular parameter meaningless. An output prediction is then re-run and the difference in performance is defined as a share of the performance for which the parameter is necessary, namely, the parameter's contribution to the prediction. Further, different dimension reduction operations may be applied to different models, even with respect to a same production run.

The above ensemble-based modeling provides for enhanced predictive accuracy.

Preferably, the model or model ensemble is periodically re-trained using historical data.

Delivering Predictions Across Each Phase of the Culture

As noted above, one or more types of predictions are generated to facilitate the quality control recommendation(s). For example, one prediction indicates that the current production run is expected to fail, in which case the quality control recommendation is a recommendation to terminate the current production run early. In another use case, the prediction is an end day for the current production run being successful and is based on a given value of at least one parameter being reached, in which case the quality control recommendation is a recommendation to terminate the current production run on the end day. As another example use case, the instance of the machine learning model generates a list of parameters and their associated contribution to the prediction, and wherein the prediction identifies at least one parameter in the list whose adjustment is expected to enable early completion of the current production run; in such case, the quality control recommendation is a recommendation to adjust the at least one parameter in the list according to an identified value. Of course, it is not required that each type of prediction be made for a particular production run.

Figure 5:
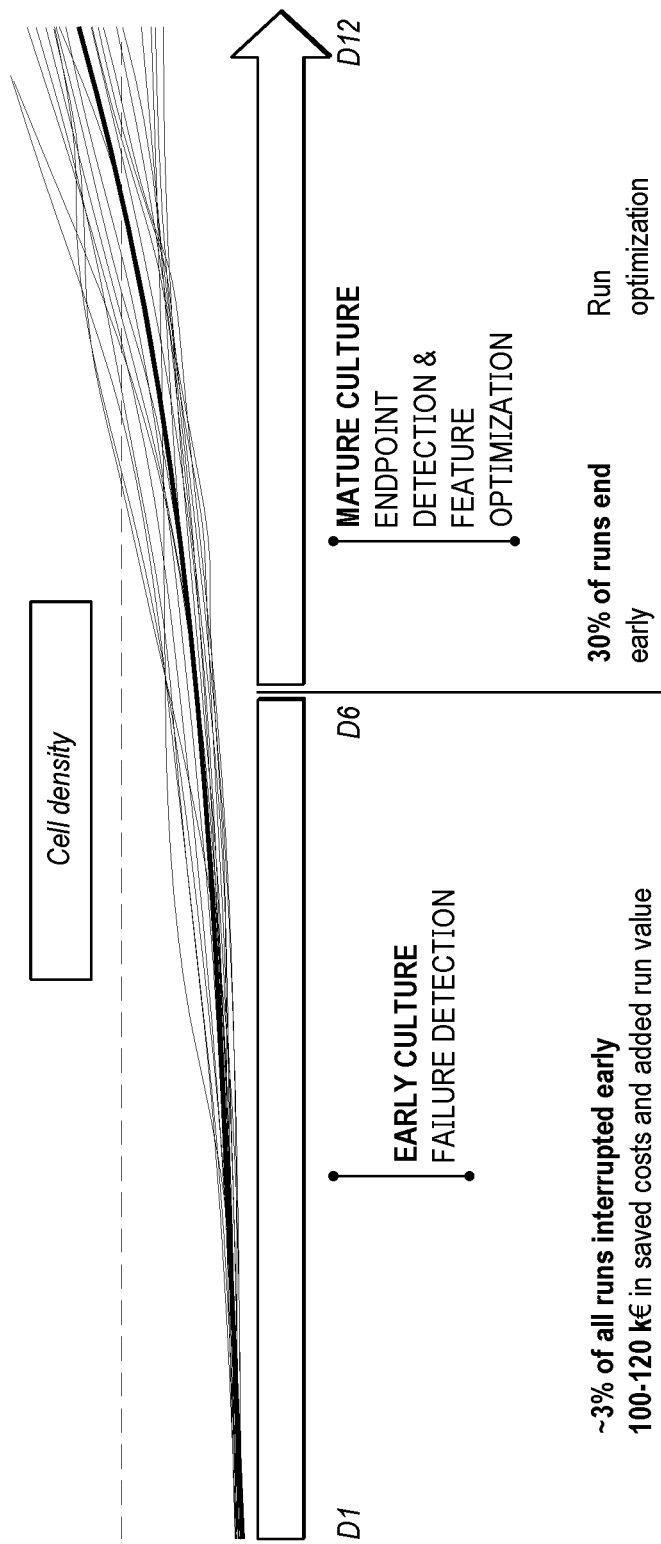
FIG. 5 depicts a graph of cell density predicted over a sample production run.

FIG. 5 depicts a timeline of a production run for a culture for the process shown in FIG. 2. Day one (1) (D1) is shown on the left and the anticipated endpoint (Day twelve (D12)) is shown on the right. The top portion of the chart depicts the cell density across numerous production runs as evidenced in the historical data. As depicted, the techniques of this disclosure enable the timeline to reflect both early culture failure detection (e.g., at or near D3), as well as mature culture endpoint detection and feature optimization (e.g., about D7). Using the techniques herein, and using cell density as a predictor (in a non-limiting example), some percentage of runs are interrupted early, as they are predicted to be failures. Interrupting a run early in its lifecycle can save significant costs and run value. As also depicted, some not-insignificant percentage of runs are predicted to be successful and to end early (in this example, at or about D7); in this manner, and by careful endpoint detection, timing optimizations can then be implemented to enable further production value benefits. In addition, and as described above, the techniques herein enable overall run optimization by enabling identification of one or more parameters that contribute to successful and (early endpoint) detection.

Process Deployment

To deploy a solution on a process line (e.g., in a bioreactor), the one or more machine learning models are trained on the historical production data that typically includes the process parameters as defined above. Of course, the nature and type of process parameters used may vary. The data may also include production (bioreactor) control information. Once the model (or model ensemble) is trained, it is deployed into production. In one example implementation, the model or model ensemble is trained in a cloud or other network-accessible compute environment, and thereafter the model is instantiated and run as a binary on computing resources within the physical production environment. The model may be instantiated in a container-type environment (e.g., a Docker image) and physically delivered to and hosted within the local production environment. In an alternative, both the training (model production) and real-time prediction are done remotely from the production environment. In another embodiment, both the training and real-time prediction occur on-premises. Typically, a hybrid deployment approach is used.

Once a prediction is used to generate a quality control recommendation, the quality control recommendation is applied to control a workflow associated with a current production run. The nature of the control typically depends on the type of prediction that has been made. In the simple case where the prediction indicates that the current production run is expected to fail, the control executes tooling to terminate the production run, e.g., by shutting down the bioreactor/fermenter, issuing appropriate notification(s) to affected systems, capturing data in a log file, or the like.

More generally, the notion of applying the quality control recommendation to control the workflow assumes that the bioproduction is being controlled by one or more automation systems. Representative automation systems include automated bioprocess handling systems, alerting systems, and various Advanced Process Control (APC) techniques and technologies implemented within the bioproduction facility. How a particular prediction generated for control purposes depends on the bioreactor/fermenter, and the particular production process. Thus, as in the example above, the prediction is used to initiate an interdiction, which stops the bioreaction or otherwise interrupts some processing operation so that the bioreaction/fermentation does not proceed further. In an alternative, the bioprocessing continues but the prediction (quality control recommendation) enables one or more parameters or process variables to be tuned dynamically, e.g., via the APC mechanisms, Statistical Process Controls (SPCs), Run-to-Run (R2R) Controls, Fault Detection and Classification (FDC) Controls, or the like. In another example, the prediction is used to drive back-end systems such as notification, logging, reporting, and the like. Generalizing, the techniques herein provide real-time predictions (e.g., the quality control recommendations) that are then integrated into the existing bioproduction workflow, preferably with the prediction(s) (recommendations) driving the back-end workflow or other tooling changes in an automated manner, thereby improving the underlying process control systems within the bioproduction facility.

Example

In an example use case, the bioreactor process is a pulmonary cell culture for viral vector production (vaccine), and the objective was to build a model able to predict Viable Cell Density (VCD) for any given day of the culture (in this case, a 14 d total culture time). To this end, twenty features were measured daily at the culture and cell level. The process variables were pH, and temperature. Metabolic activity variables were glucose and glutamine consumption, glutamate and lactate production, osmolality, and oxygen flow. As noted, the target was Viable Cell Density (VCD). A first model classified cultures as successful, or failed, i.e., did the culture reach a given VCD threshold (yes/no). A second model predicted when a VCD threshold would be reached for successful cultures. The model architecture included a Gaussian process combined with autoencoders. For training, several years of production data from several different production sites was utilized, including both development and production runs. The following results were obtained: 90% of failed runs were identified correctly on day 4 of the culture, and 100% by day 5, and 30% of successful runs were ended one (1) day early without significant impact on final VCD. The example validated that failed runs could be detected and interrupted earlier to free-up production capacity, and that relevant successful runs could be ended earlier to reduce cycle time. The approach also enable production parameter optimizations to be identified and applied. The overall benefit in this example was 10-15% added production capability per bioreactor.

The techniques herein have significant advantages. The solution provides optimal and stable predictive performance in any type of production environments, and is able to model complex systems (the bioreactor and its biological process) reliably, and in a scalable, highly-available manner. Predictions are robust, even where data is limited. Further, the approach seamlessly integrates readily into the process environment (with no ramp-up required) and maintains accurate and timely performance predictions even as changes are made in the production process. The high predictive performance is carried out without requiring changes to the production system or testing protocols, and irrespective of the density or sparsity of the process data that is made available to the system. A typical prediction is simple to absorb and make actionable. For each unit and in real-time, engineers within the production environment know if a particular culture is likely to succeed or fail, and when. The approach gives manufacturers visibility for every culture day of their manufacturing process at scale as soon as the model is deployed, enabling both significant yield improvements and cost savings. By leveraging deep learning and the ensemble approaches described, the development and deployment of advanced models is enabled, even for limited and unbalanced data. Deep learning as has been described enables the system to model the non-linear systems, extracting features and generalizing to establish complex relationships between and among multiple parameters represented in the process data.

Enabling Technologies

Typically, the predictive operating system of this disclosure is managed and operated "as-a-service" by a service provider entity. In one embodiment, a computing platform on which the predictive operating system executes is accessible over the publicly-routed Internet at a particular domain, or sub-domain. The platform is a securely-connected infrastructure (typically via SSL/TLS connections), and that infrastructure includes data encrypted at rest, e.g., in an encrypted database, and in transit. The computing platform typically comprises a set of applications implemented as network-accessible services. One or more applications (services) may be combined with one another. An application (service) may be implemented using a set of computing resources that are co-located or themselves distributed. Typically, an application is implemented using one or more computing systems. The computing platform (or portions thereof) may be implemented in a dedicated environment, in an on-premises manner, as a cloud-based architecture, or some hybrid. Although typically the platform is network-accessible, e.g., via the publicly-routed Internet, the computing system may be implemented in a standalone or on-premises manner. In addition, one or more of the identified components may interoperate with some other enterprise computing system or application.

One or more functions of the computing platform of this disclosure may be implemented in a cloud-based architecture. As is well-known, cloud computing is a model of service delivery for enabling on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The platform may comprise co-located hardware and software resources, or resources that are physically, logically, virtually and/or geographically distinct. Communication networks used to communicate to and from the platform services may be packet-based, non-packet based, and secure or non-secure, or some combination thereof.

More generally, the machine learning techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a standalone machine, or across a distributed set of machines.

The techniques herein find practical application in improving operations associated with bioproduction processes, bioreactors and fermenters, and associated control systems and devices.

There is no requirement that the above-described methodology be practiced in any particular bioreactor or fermenter. In the bioreactor use-case, representative bioreactors are single-use bioreactors, such as 5 L for development (e.g., Pall Allegro™ 2D Biocontainer 5 L), and 2000 L for production (e.g., Pall Allegro STR 2000). Bioreactors of this type typically record a range of variables, ranging from temperature, pressure, pH, $O_2$ saturation, $CO_2$ saturation, osmolarity, and turbidity, among others. In the fermentation use-case, representative machines include, e.g., Sartorius Biostat™. This type of machine records parameters such as pH, turbidity, and temperature (which is a controlled parameter).

What we claim is as follows:

1. A method to provide real-time quality control of a culture for bioproduction, wherein the culture takes place in one of: a bioreactor, and a fermenter, comprising:
   receiving real-time process data for one or more of a set of parameters for a current production run;
   based at least in part on the received real-time process data, generating a prediction using an instance of a machine learning model, the instance being uniquely associated to a particular culture day and having been trained on process data from past production or development runs;
   applying an output generated from the instance of the machine learning model as an input to a first ancillary model, the ancillary model generating an output;
   feeding back the output of the ancillary model as an input to the instance of the machine learning model;
   based on the prediction, providing a quality control recommendation for the current production run; and
   applying the quality control recommendation to control a workflow associated with the current production run.

2. The method as described in claim 1 wherein the first ancillary model facilitates a feature analysis to identify one or more of the set of parameters whose adjustment is expected to enable early completion of the current production run.

3. The method as described in claim 1 further including executing a second ancillary model before the instance of the machine learning model, the second ancillary model receiving historic data and generating an output.

4. The method as described in claim 3 further including feeding the output from the second ancillary model as an input to the instance of the machine learning model.

5. The method as described in claim 3 wherein the second ancillary model is a Gaussian Mixed Model (GMM).

6. The method as described in claim 3 wherein the output of the second ancillary model identifies one or more successful production runs.

7. The method as described in claim 4 wherein the output of the second ancillary model is a set of distribution values associated with the one or more successful production runs, the set of distribution values being the input to the instance of the machine learning model.

8. The method as described in claim 1 wherein the prediction indicates that the current production run is expected to fail, and wherein the quality control recommendation is a recommendation to terminate early the current production run.

9. The method as described in claim 1 wherein the prediction is an end day for the current production run being successful and is based at least in part on a given value of at least one parameter being reached, and wherein the quality control recommendation is a recommendation to terminate the current production run on the end day.

10. The method as described in claim 1 wherein the instance of the machine learning model generates a list of parameters and their associated contribution to the prediction, wherein the prediction identifies at least one parameter in the list whose adjustment is expected to enable early completion of the current production run, and wherein the quality control recommendation is a recommendation to adjust the at least one parameter in the list according to an identified value.

11. The method as described in claim 1 wherein the instance of the machine learning model is independent of any other instance of the machine learning model and is trained using the process data from past production or development runs for each culture day preceding the particular culture day.

12. The method as described in claim 1 wherein the machine learning model is a feedforward neural network.

13. The method as described in claim 1 wherein the prediction is associated with a confidence measure.

14. The method as described in claim 1 further including training the machine learning model.

15. The method as described in claim 14 wherein the machine learning model is trained remotely from the bio-production and the prediction is generated and provided on-premises.

16. The method as described in claim 1 wherein the machine learning model instance for a particular culture day is trained on the historical process data received with respect to one or more culture days occurring prior to the particular culture day.

17. The method as described in claim 1 wherein the machine learning model instance for a particular culture day is trained on the historical process data received for each of the culture days occurring prior to the particular culture day.

* * * * *